US009211056B2

(12) United States Patent  
Geisser et al.

(10) Patent No.: US 9,211,056 B2  
(45) Date of Patent: Dec. 15, 2015

(54) MEDICAL APPARATUS TO SUPPORT AN ENDOSCOPIC INVESTIGATION

(75) Inventors: Romana Geisser, Blumberg (DE); Clemens Rebholz, Uhldingen-Muehlhofen (DE); Fritz Hensler, Neuhausen (DE); Peter Schwarz, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 789 days.

(21) Appl. No.: 12/956,896

(22) Filed: Nov. 30, 2010

(65) Prior Publication Data

US 2011/0144435 A1  Jun. 16, 2011

(30) Foreign Application Priority Data

Nov. 30, 2009  (DE) .......................... 10 2009 056 108

(51) Int. Cl.
| | |
|---|---|
| *A61B 1/00* | (2006.01) |
| *A61B 1/04* | (2006.01) |
| *A61B 1/06* | (2006.01) |
| *A62B 1/04* | (2006.01) |
| *B60Q 3/04* | (2006.01) |

(Continued)

(52) U.S. Cl.
CPC ............ *A61B 1/042* (2013.01); *A61B 1/00048* (2013.01); *A61B 1/0669* (2013.01); *A45C 9/00* (2013.01); *A45C 2200/15* (2013.01); *A61B 1/00128* (2013.01); *A61B 1/015* (2013.01); *A61B 2560/0431* (2013.01)

(58) Field of Classification Search
USPC ......... 600/101, 132, 146, 160–181, 300, 301, 600/109–113, 118, 223, 245–249; D24/137, 138, 186; 362/257–311.15, 362/362, 572–575; 348/65–76

See application file for complete search history.

(56) References Cited

U.S. PATENT DOCUMENTS 4,489,712 A * 12/1984 Ohshima ....................... 600/158  
4,539,586 A *  9/1985 Danna et al. ................... 348/75

(Continued)

FOREIGN PATENT DOCUMENTS

| CN | 2549897 Y | * | 5/2003 | .............. A61B 1/04 |
|---|---|---|---|---|
| CN | 2549897 Y |   | 5/2003 | |

(Continued)

OTHER PUBLICATIONS

Karl Storz Product Flyer: "Kompact Leicht Portable Pack Digital"; published in Aug. 2010; 3 pages.

(Continued)

*Primary Examiner* — Ryan Henderson  
(74) *Attorney, Agent, or Firm* — Whitmyer IP Group LLC

(57) ABSTRACT

A medical apparatus to support an endoscopic investigation that includes a housing with a base surface, a front surface and a rear surface, and a light source that is positioned in the housing to generate light to illuminate an object that is to be investigated with an endoscope. In addition the medical apparatus includes a coupling device to couple a proximal end of an endoscope on the medical apparatus and to transmit light from the medical apparatus to the endoscope. The medical apparatus includes a screen, which is positioned on the front surface of the housing to observe an image taken by means of the endoscope, where the front surface and rear surface are each inclined toward the rear at an angle between 5 and 15 degrees with respect to a plane perpendicular to the base surface.

15 Claims, 6 Drawing Sheets

(51) Int. Cl.
*A45C 9/00* (2006.01)
*A61B 1/015* (2006.01)

(56) References Cited

U.S. PATENT DOCUMENTS

| | | | |
|---|---|---|---|
| 4,589,404 A * | 5/1986 | Barath et al. | 600/108 |
| 5,348,268 A | 9/1994 | Klein | |
| 5,365,058 A * | 11/1994 | Wheeler et al. | 250/216 |
| 5,526,249 A * | 6/1996 | Karasawa et al. | 362/362 |
| 5,885,214 A | 3/1999 | Monroe et al. | |
| 7,946,981 B1 * | 5/2011 | Cubb | 600/194 |
| 2004/0204628 A1 | 10/2004 | Rovegno | |
| 2007/0070340 A1 * | 3/2007 | Karpen | 356/241.1 |
| 2008/0207996 A1 * | 8/2008 | Tsai | 600/112 |
| 2008/0228036 A1 | 9/2008 | Suzuki et al. | |
| 2009/0116260 A1 | 5/2009 | Rovegno | |
| 2009/0147251 A1 * | 6/2009 | Suzuki | 356/241.1 |

FOREIGN PATENT DOCUMENTS

| | | | | |
|---|---|---|---|---|
| DE | 19944726 A1 | | 5/2000 | |
| DE | 20309956 U1 | | 12/2003 | |
| DE | 20309956 U1 | * | 2/2004 | ............... A61B 1/00 |
| JP | 61075315 A | * | 4/1986 | ............... A61B 1/00 |
| JP | 64076826 A | * | 3/1989 | ............... A61B 1/00 |
| JP | 05297284 A | * | 11/1993 | ............... A61B 1/00 |
| JP | 08140929 A | * | 6/1996 | ............... A61B 1/00 |
| JP | 2004321243 A | * | 11/2004 | ............... A61B 1/00 |
| JP | 2005102751 A | * | 4/2005 | ............... A61B 1/00 |
| WO | 9715144 A1 | | 4/1997 | |
| WO | WO 9715144 A1 | * | 4/1997 | ............... H04N 7/18 |
| WO | 2004041096 A2 | | 5/2004 | |

OTHER PUBLICATIONS

Karl Storz Product Flyer: "Techno Pack (tm)—Die Mobile Lösung"; published in 2000; 2 pages.
Storz Brochure; Karl Storz—Endoskope—The Diamond Standard; "Der Karl Storz Tele Pack Kompakt, Transportabel, Universell"; www.karlstroz.com; Aug. 2009; 12 pages.
European Search Report; Application No. EP 10 01 4337; Issued: Mar. 8, 2011; 4 pages.
Storz Brochure; Karl Storz GmbH & Co. KG; Karl Storz—Endoskope Industrial Group; "Techno Pack X mit Multipoint-Messsystem"; www.karlstorz.com; Nov. 2006; 2 pages.

* cited by examiner

MEDICAL APPARATUS TO SUPPORT AN ENDOSCOPIC INVESTIGATION

CROSS-REFERENCE TO RELATED APPLICATIONS

The present application claims priority of German patent application No. 10 2009 056 108.0 filed on Nov. 30, 2009, the content of which is incorporated herein by reference.

FIELD OF THE INVENTION

The present invention relates to a medical apparatus to support an endoscopic investigation, having a light source to produce light to illuminate an object that is to be examined with an endoscope and also having a screen to observe an image captured by means of the endoscope.

BACKGROUND OF THE INVENTION

For a long time, endoscopic medical investigations and procedures were conducted almost exclusively in operating rooms or other medical treatment areas. The light sources required for the endoscopic investigations were placed, for example, in racks or shelves that were firmly standing or movable on wheels. With the use of a video camera on the proximal end of the endoscope and later with the introduction of the video endoscope with a video camera on the distal end of the endoscope, a screen was added to display the images captured by the video camera, said screen being set up or suspended in an appropriate place. For documentation purposes, the images taken by the video camera were also fed to a storage unit (video recorder, DVD burner, hard disk drive or the like), which was set up as an additional separate device in the treatment area.

Endoscopic investigations and procedures of medical or non-medical nature alike were increasingly conducted outside of treatment areas installed and equipped for the purpose. Examples include endoscopy in emergency medicine, in veterinary medicine, and a major part of non-medical endoscopy. For applications of this kind, devices were developed that include a light source and image screen and thus make possible endoscopic investigations in combination with a video endoscope or an endoscope with camera head on the proximal end.

These conventional integrated devices, however, have a series of disadvantages. In particular, equipped with foldable screens or feet, they can lack desirable robustness and stability.

SUMMARY OF THE INVENTION

It is an object of the present invention to provide an improved medical apparatus to support an endoscopic investigation.

This object is achieved through the content of the independent claims.

Refinements are indicated in the dependent claims.

Embodiments of the present invention are based on the idea, in a medical apparatus to support an endoscopic investigation, of inclining the front surface and rear surface toward the rear by an angle between 5 and 15 degrees with respect to a plane perpendicular to the base surface, in particular by an angle between 7 and 10 degrees. In this embodiment an angle between 8 and 9 degrees has proved particularly useful. Inclining the front surface with its integrated screen, in many practical applications in which the medical apparatus stands, for instance, on a table or on the floor of a stall, improves readability of the screen. Simultaneously, with the aforementioned inclination of the front surface and rear surface with respect to a plane perpendicular to the base surface, it is possible to achieve good stability of the medical apparatus.

Conventionally, to achieve stability a housing, for instance, in the form of a horizontal rectangular solid, is configured in which one of the two largest rectangular outer surfaces forms the base surface or stand surface. Alternatively, unfoldable feet or slats can be provided to widen the base. The present invention is based on the recognition that a housing with approximately the shape of a standing rectangular solid can have a strong stability even with a slight inclination of the front surface and rear surface toward the rear. As a result of the slight inclination toward the rear, the center of gravity of the screen, which contributes significantly to the total mass of the medical apparatus, is pushed toward the rear and thus in the direction toward the center of the base surface. Because of a preferred arrangement of heavy components of the medical apparatus in the lower half, or better in the lower third, of the housing of the medical apparatus, their centers of gravity are displaced inconsequentially toward the rear by the inclination of the housing.

The present invention thus provides a medical apparatus to support an endoscopic investigation, which makes possible good readability of the image screen even without the ability to pivot an integrated screen by means of a hinge. At the same time the approximately rectangular shape of the housing ensures compactness, enhancing its portability, while the medical apparatus is made more stable thanks to the balanced positioning of the center of gravity despite, or in fact because of, the slight inclination of the front end toward the rear, in view of the heavy screen.

A medical apparatus to support an endoscopic investigation includes a housing with a base surface, a front surface and a rear surface, and a light source that is positioned in the housing to generate light to illuminate an object that is to be investigated with an endoscope. In addition, the medical apparatus to support an endoscopic investigation includes a coupling device for direct or indirect coupling of a proximal end of an endoscope to the medical apparatus and to transmit light from the medical apparatus to the endoscope and a screen that is positioned on the front surface of the housing to observe an image captured by the endoscope, while the front surface and rear surface are each inclined toward the rear at an angle between 5 and 15 degrees with respect to a lane er endicular to the base surface. The base surface (for example, apart from the foot and the optional fastening devices described hereinafter) is the essentially flat area of the outer surface of the housing that is provided and configured to be positioned essentially parallel to a tabletop, a floor or other surface on which the medical apparatus stands for the application foreseen for the medical apparatus. The front surface likewise is, in particular, essentially flat. Departures from a completely flat shape of the front surface are due, for instance, to keys or push buttons, other operational elements, electric outlets or a somewhat recessed position of the screen. However, these departures, in a preferred embodiment, typically amount to only a few millimeters. In the embodiment described below, the keys on the front surface extend less than 3 mm beyond a flat border surrounding the screen on at least three sides, and the front surface of the screen is recessed from the aforementioned border by less than 3 mm. The rear surface is the largest, essentially flat continuous or non-continuous portion of the surface of the housing on its rear. Aside from this essentially flat portion, the rear of the housing can include recesses and openings in particular. The rear surface can have minor departures from the flat shape, for example in the form of raised or incised script or other symbols, in the form of ventilation grids or apertures, coverings inserted flush or essentially flush, or recesses in which screw heads are embedded.

The angle at which the front surface and rear surface are inclined with respect to a Mane perpendicular to the base surface, or the departure of the angle between the front surface and base surface from 90 degrees, is in particular in the range of 7 to 10 degrees or in the range of 8 to 9 degrees. As already stated, this inclination of the front surface and thus of the screen on the front surface improves the readability of the screen. At the same time, the screen's relatively highly situated center of gravity (approximately in the center of the screen) is moved to the rear owing to the inclination of the front surface, and thereby the stability of the medical apparatus can be improved.

In a medical apparatus as described above, the coupling device for coupling a proximal end of an endoscope directly or indirectly to the medical apparatus is configured by means of a light conductor cable. The coupling device can be positioned at an angle between 50 and 70 degrees to the front surface. The angle between 50 and 70 degrees is, in particular, the angle between a direction in which a coupling of a light conductor cable or of a proximal end of an endoscope can be inserted into the coupling direction and the normal of the front surface.

If this angle is zero degrees, the coupling of the light conductor cable standing precisely in the forward direction or parallel to the normal of the front surface of the housing or the correspondingly aligned proximal end of the endoscope can make it difficult to operate the switches and keys on the front surface. If the angle is 90 degrees and the coupling of a light conductor cable or the coupling on the proximal end of an endoscope, that is, from the side, is to be inserted into the coupling device on the housing of the medical apparatus, the coupling or light conductor cable or the proximal end of the endoscope stands far off to the side. In such cramped conditions, which can often occur in emergency medicine or veterinary medicine, this means not just a restriction in setting up the medical apparatus but also an increased risk of damage.

As opposed to this, an angle between 50 and 70 degrees, in particular an angle of 60 degrees, offers on the one hand a reduced lateral space requirement or an altogether more compact arrangement and on the other hand an unimpeded access to all operational elements on the front surface.

In a medical apparatus as described here, the light source occupies a space in the housing that is situated entirely in the half of the housing bordering on the base surface, in particular entirely in the third of the housing that borders on the base surface. The space occupied by the light source, in particular, borders on the base surface. The same applies to the devices for supplying the medial apparatus with electric current from a public power grid, in particular for a transformer, and for a pump, a compressor or a blower to convey a fluid. In addition to the screen, whose center of gravity is displaced by the inclination of the front surface toward the rear, the light source and devices for power supply can be the heaviest components or elements in the medical apparatus. As a result of the aforementioned arrangement of the light source, devices for power supply and pump, the compressor or blower, the inclination of the housing toward the rear—apart from the described positive effect on the center of gravity of the screen—has only a minor impact on the location of the center of gravity of the medical apparatus. The described arrangement of the light source, the devices for power supply and the pump, the compressor or blower therefore has the particular effect that good readability of the screen can be combined with good stability of the medical apparatus owing to the inclination of the front surface with the screen.

A medical apparatus as described here can comprise on the base surface a fastening device, in particular several fastening devices, to secure the housing of the medical apparatus at least either on a transport case for the medical apparatus or on a tripod or in or on a shelf or on another apparatus. The fastening device is configured, for example, to secure the medical apparatus onto an outer surface and/or onto an inner surface of a transport case. For example, the medical apparatus can be secured in a transport case in such a way that, immediately after opening the transport case, that is, without first mechanically separating the medical apparatus from the transport case, it can be used to support an endoscopic investigation. Alternatively or in addition, the fastening device can be provided to secure the medical apparatus on or in a shelf, for example a shelf in a medical treatment area.

The fastening device on the base surface of the medical apparatus is in particular a groove with dovetail-shaped or trapezoidal cross-section or with T-shaped cross-section. The groove cross-section can taper from one end of the groove to the other to have a clamping effect with a corresponding matching piece. Instead of, or in addition to, one or more grooves, it is possible to provide one or more screw threads, bayonet locks, or other devices for form-locked fastening. Instead of a device for form-locked fastening or in addition there to, one or more devices can be provided on the base surface of the housing that increase the normal force with a form-locked or friction-locked fastening of the medical apparatus onto an outer surface of a transport case, a tripod, or other apparatus. These include a vacuum friction stand, a magnetic holder, tension belt, clamping jaw and a turnbuckle The described fastening devices can make possible a reliable or easily and quickly produced and released mechanical fastening of the medical apparatus, if necessary with the corresponding complementary devices, on a transport case, a tripod or another apparatus. An additional gain in stability of the medical apparatus at low additional cost can be achieved precisely through the fastening of the medical apparatus onto a transport case, which is used in any case in many applications to transport the medical apparatus. The medical apparatus, in the form of a system composed of several components, can include, in addition to the housing with the light source, coupling device and screen, a transport case that is configured to completely contain the medical apparatus during its transport and a fastening device onto an outer surface that is complementary to the fastening device onto the base surface of the housing.

It is also possible of course for the fastening device on the base surface of the medical apparatus to be, in particular, a groove with dovetail-shaped or trapezoidal cross-section or with T-shaped cross-section. The fastening devices on a transport case, a tripod or another apparatus are correspondingly complementary.

In a medical apparatus as described here, the rear surface can include a U-shaped recess in which a fastening device is positioned to secure a battery on the medical apparatus. This battery, to supply the medical apparatus, can be coupled with it mechanically and electrically in order to be able to operate the medical apparatus in locations in which no electrical power grid is available. The recess and battery are adapted to one another, in terms of their shape and size in particular, in such a way that the battery does not extend outside the recess when it is secured in the recess on the fastening device. This means, in particular, that the battery secured on the fastening device in the recess does not extend, or not essentially, beyond the plane in which the rear surface lies or which is defined by the rear surface.

The fastening device in the recess can also be configured for an alternative fastening of the aforementioned battery or of a cooling element on the medical apparatus or to fasten the medical apparatus onto a bracket, for example a wall or ceiling bracket, a tool cart or a shelf. The fastening device, for this purpose, corresponds in particular to the VESA (Video Electronic Standard Association) standard for wall and ceiling mounting of flat screens. In particular, the fastening device includes four threaded holes at the corners of a rectangle with a lateral length of 100 mm, where each thread is an M4, M5, M6 or M8 metrical thread with a thread length of at least 10 mm. As a result of this configuration of the fastening device, the medical apparatus can be stationarily secured at many locations in which a wall or ceiling bracket is provided for a flat screen. A bracket that meets VESA standards can also be provided on a tool cart or a mobile or stationary shelf for a medical treatment area.

In addition, a cooling element can be positioned in the recess to expel heat effluents from the light source integrated into the medical apparatus, from a device for power supply integrated into the medical apparatus, or from another device integrated into the medical apparatus. The cooling element can be combined with the fastening device. In addition, the cooling element can be removably secured in the recess on the medical apparatus by means of the fastening device. For example, the threaded holes in accordance with VESA can be on or close to the corners of the cooling element. In particular when the fastening device is configured in such a way that a battery or a wall or ceiling bracket mechanically connected with the medical apparatus is somewhat at a distance from the cooling element (for example, a few millimeters, in particular 2 to 10 mm), a battery removably secured on the fastening device or a wall or ceiling bracket secured on the fastening device only slightly restricts an air current through the cooling element and its cooling effect. In addition, a warming of the battery, particularly with a modern lithium-ion battery, can have a positive effect on the available current and the available energy. Heat transmission onto a wall or ceiling bracket can reinforce the cooling effect. The combined arrangement of the fastening device and the cooling element is thus advantageous not only for its overall reduced space requirement.

In a medical apparatus with a fastening device as described here, the fastening device can have a tapered shape into which a keyhole-shaped recess can be suspended in a housing wall of a battery, where the battery includes a catch-lock groove that allows a catch-locking connection with the battery. The tapered shape on the fastening device, like the keyhole-shaped recess in the housing wall, can be manufactured at minor cost but allows, particularly in combination with the catch-lock connection, a reliable mechanical connection between the medical apparatus and a battery that can be easily established and released.

A medical apparatus as described here can include on the rear of the housing a cable retainer for storing a power supply cable or other cables. Conventionally, as a rule, a particular location in the transport case is set aside for cables. As a rule a cable retainer is provided on an appliance only if the appliance is expected to be used without a transport case. Experience has shown, however, that it is advantageous, also with a medical apparatus that is foreseen and configured for transport in a transport case, if the cables can be stored on a cable retainer on the medical apparatus itself. In particular, immediately after removal of the medical apparatus from the transport case, said case can be closed again in order to secure the medical apparatus outside on the transport case. Only then can the cable be taken from the cable retainer on the medical apparatus. Therefore the cable must not be put away in the meantime, so that it could be misplaced or damaged. The cable retainer on the rear of the housing of the medical apparatus thus allows a more rapid and more precise working sequence in setting up or putting into operation the medical apparatus.

Some properties of the medical apparatuses described here, in particular the inclination of the front surface with the screen toward the rear and the described arrangement of the light source and/or of the device for power supply, make possible a low placement of the center of mass of the medical apparatus. In particular, the center of mass is at a distance from the base surface of the housing equal to at most one-third or at most one-fourth of the total height of the housing. This allows a particularly high stability of the medical apparatus and reduces the risk of damage from tipping over.

A medical apparatus as described here includes in particular a retaining device, partly integrated into the housing, for storing a fluid to be used in an endoscopic investigation. Such retaining devices, for instance for glass or plastic bottles, conventionally extend outside the housing, for example in the form of a basket or beaker. To absorb the resulting forces and moments, a conventional retaining device must be of correspondingly strong dimensions and have a correspondingly large mass. Because of the at least partial integration into the housing, it can be executed with small mass. The at least partial integration of the retaining device into the housing, in addition, reduces the risk of damage to the retainer device and/or the vessel.

A battery for a medical apparatus to support an endoscopic intervention includes a housing wall, a keyhole-shaped recess in the housing wall for mechanical coupling of the battery with a fastening device of the medical apparatus, and a catch-lock device to engage in a catch-lock groove on the medical apparatus.

BRIEF DESCRIPTION OF THE DRAWINGS

Embodiments are explained further hereinafter as examples, with reference to the appended drawings.

DETAILED DESCRIPTION OF THE INVENTION

Figure 4:
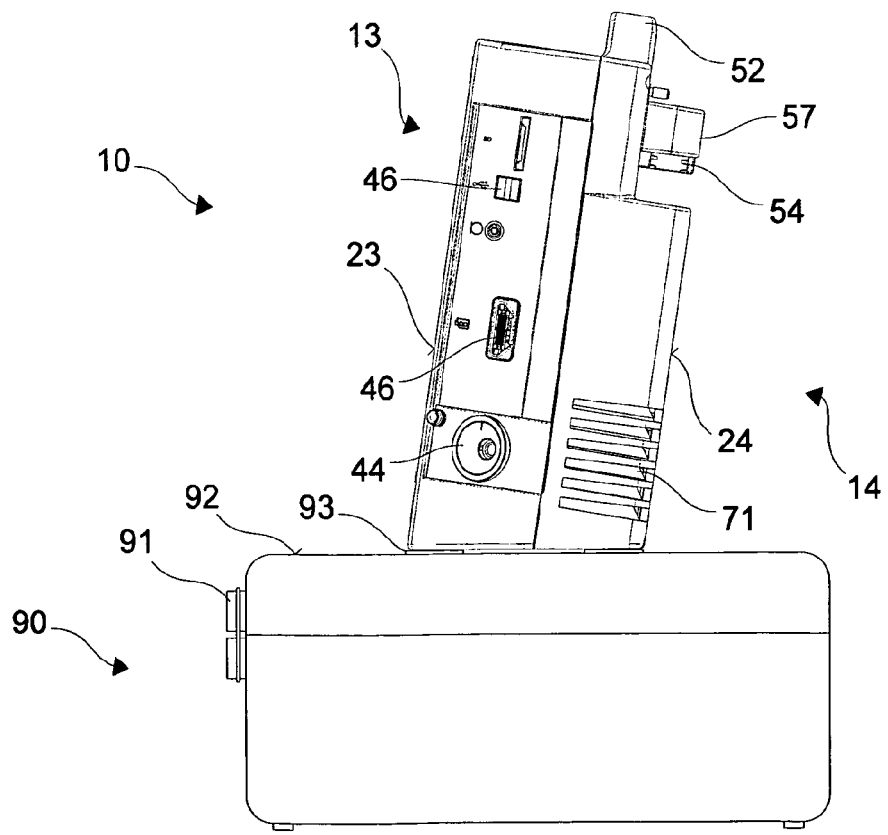
FIG. 4 shows a schematic axonometric depiction of the medical apparatus from the right.
Figure 5:
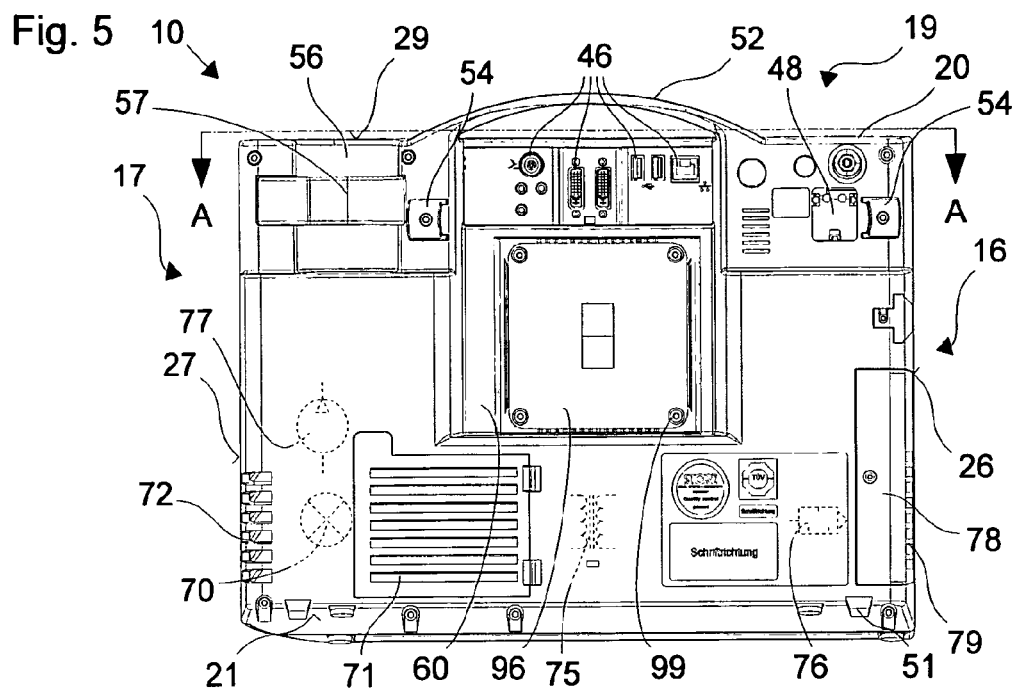
FIG. 5 shows a schematic axonometric depiction of the medical apparatus from the rear.
Figure 6:
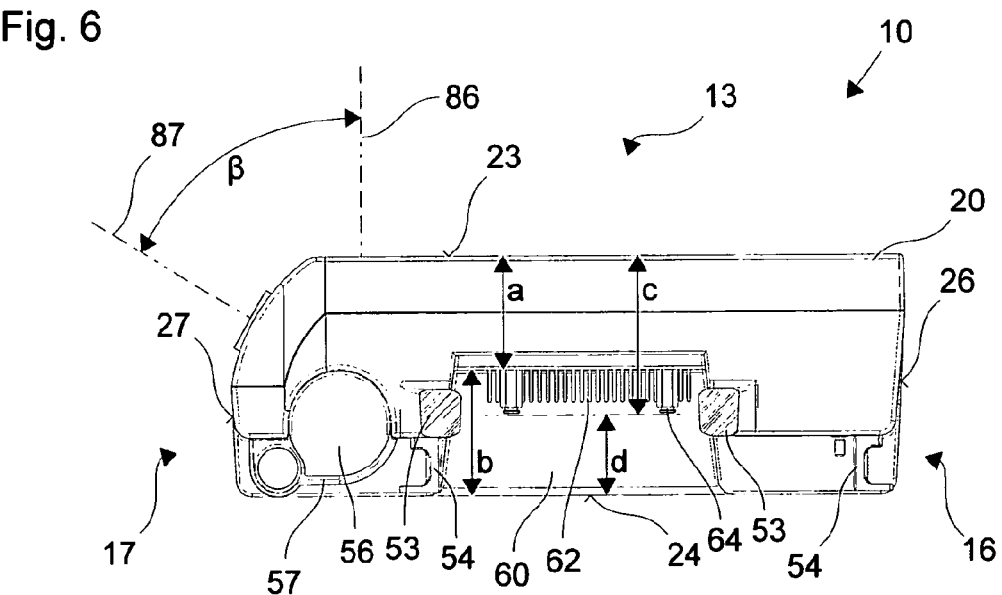
FIG. 6 shows a schematic axonometric depiction of the medical apparatus from above.

FIGS. 1 through 8 show schematic axonometric depictions of a medical apparatus 10 from various perspectives or viewing angles. FIG. 6 actually shows a depiction of a section along the plane A-A shown in FIG. 5, which however cuts through only one handle so that characteristics under it are visible. The indications of direction used hereinafter—"forward," "backward," "left," "right," "above" or "below"—refer here to the expected use of the medical apparatus 10 in which it usually stands on a fixed horizontal basis in such a way that medical personnel can interact optimally with user interfaces on the front of the medical apparatus.

Figure 7:
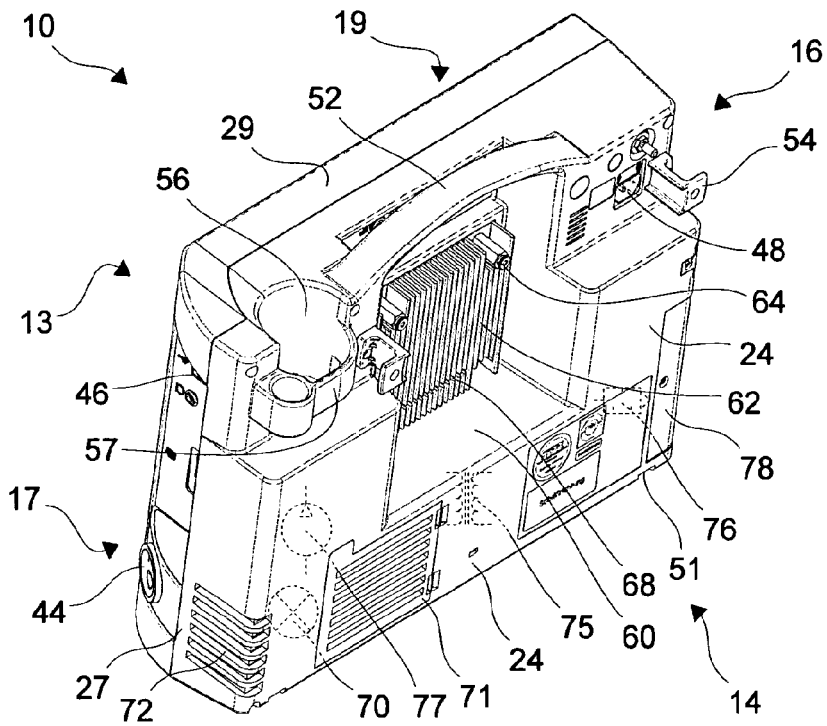
FIG. 7 shows a schematic axonometric depiction of the medical apparatus from a diagonal direction.
Figure 8:
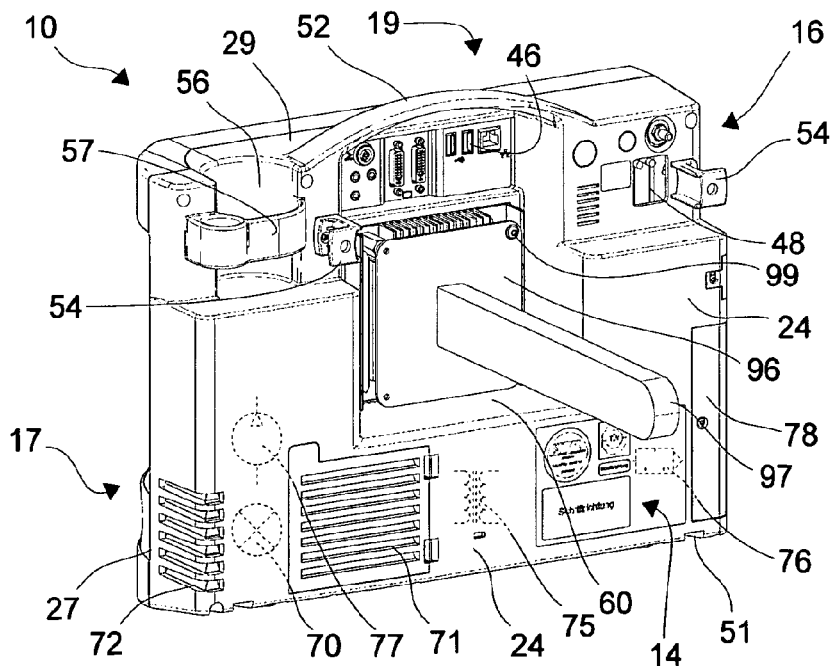
FIG. 8 shows another schematic axonometric depiction of the medical apparatus from a diagonal direction.

The medical apparatus 10 comprises an underside 11, a front side or front 13, a rear 14, a left side 16, a right side 17, and a top side 19. The left side 16 is at the left when viewed by a person using or operating the medical apparatus 10. The front 13 of the medical apparatus 10 is shown in particular in FIG. 1, the rear 14 in particular in FIGS. 2 through 5. The left 16 of the medical apparatus 10 is shown in particular in FIG. 3, the right side 17 in FIG. 4. FIG. 6 shows the medical apparatus 10 from above; FIGS. 7 and 8 each show at least parts of the rear 14, the right side 17 and the top side 19.

The medical apparatus 10 includes a housing 20 with a base surface 21, a front surface 23, a rear surface 24, a left side surface 26, a right side surface 27 and a top surface 29. The front surface 23 of the housing 20 is essentially flat and includes a rectangular screen 32 or its transparent surface, which is surrounded by an L-shaped, U-shaped or rectangular frame 33 on two, three or all sides. Positioned inside the frame 33 are an on/off switch 34, several keys 36 including cursor keys 38 and control lamps 39, which display for example the operational status of the medical apparatus 10. Departures of the spatial shape of the front surface 23 from a plane can result from the screen 32, the on/off switch 34, the keys 36, cursor keys 38 and the control lamps 39, which in each case can be positioned to be flush-flat, raised or recessed with respect to the frame 33. These departures in the embodiment illustrated here amount only to a few millimeters, in particular to less than 5 mm.

The rear surface 24, as can be recognized in particular in FIGS. 2, 4, 7 and 8, with its U-shape occupies a major part of the rear 14 of the housing 20. The rear surface 24 is essentially flat; departures from an ideally level shape occur where script or other signs are present, either raised or recessed, as well as with flaps, ventilating screens and screw-holes as described hereinafter. These departures, however, amount only to a few millimeters, in particular to less than 5 mm, and/or occupy only small partial areas. In addition to the essentially flat rear surface 24, the rear 14 of the medical apparatus 10 or of its housing 20, however, includes other surfaces that are set back with respect to the dominant rear surface 24. This can be seen in particular in FIGS. 7 and 8.

Figure 1:
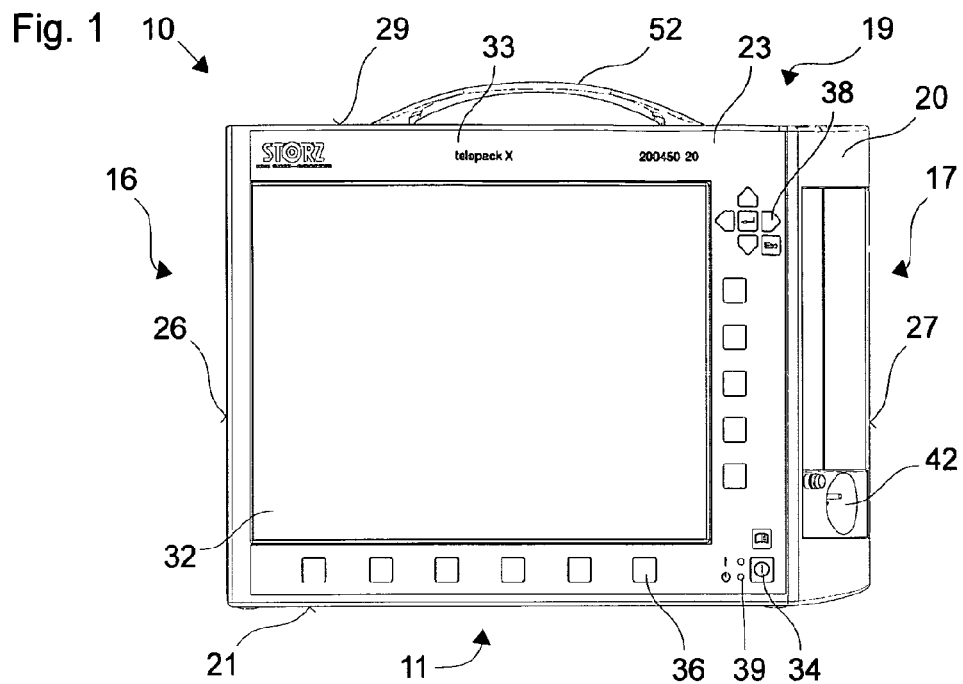
FIG. 1 shows a schematic axonometric depiction of a medical apparatus from the front.
Figure 2:
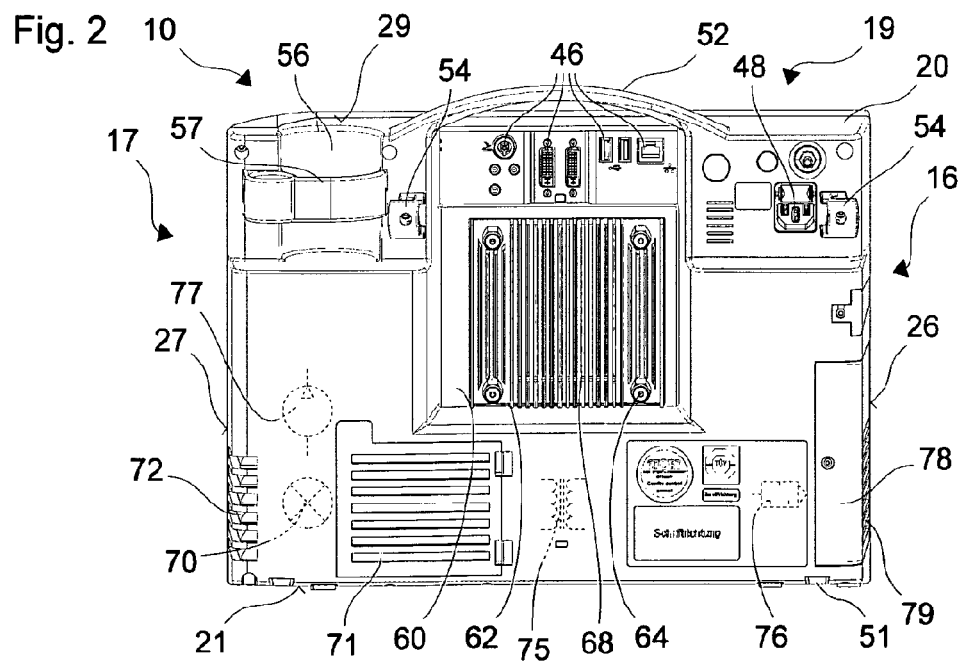
FIG. 2 shows a schematic axonometric depiction of the medical apparatus from the rear.
Figure 3:
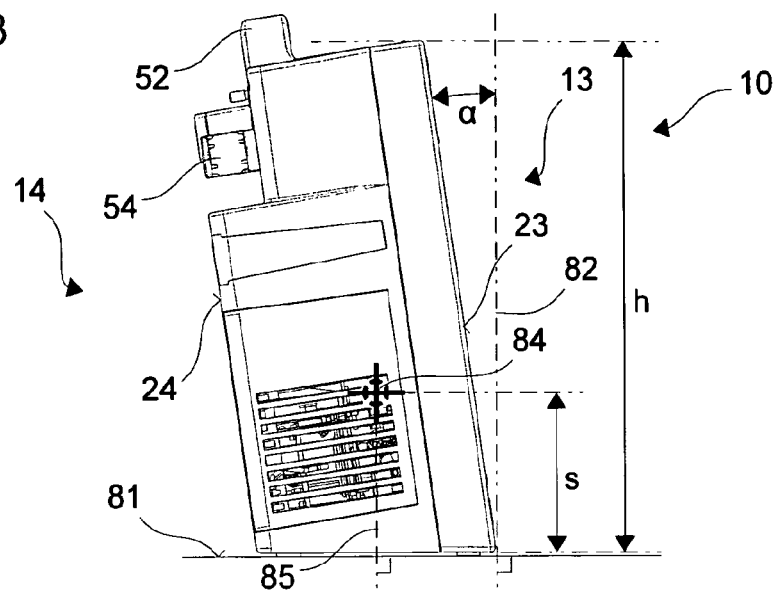
FIG. 3 shows a schematic axonometric depiction of the medical apparatus from the left.

The left side surface 26 of the housing 20 is shown in FIG. 3. It can be seen in particular in FIG. 6 that the left side surface 26 of the housing 20 is essentially flat and arranged approximately at a right angle to the front surface 23 and to the rear surface 24. The right side surface 27 is shown in FIG. 4. It can be seen in particular in FIG. 6 that the right side surface 27 includes a domed portion that continues at an angle clearly less than 90 degrees into the front surface 23.

Positioned in the domed portion of the right side surface 27 of the housing 20 is a coupling device 42 (compare FIG. 1) into which an adapter device 44 can be inserted (compare FIGS. 4, 7). A coupling on one end of a light conductor cable can be coupled by the adapter device 44 with the coupling device 42 in order to transmit light from the medical apparatus to an endoscope. After exchanging the adapter device 44 with another adapter device, which is not illustrated in the drawings, a coupling on a proximal end of an endoscope can be directly coupled with the coupling device 42 by means of this other adapter device.

As can be recognized in particular in FIGS. 2, 4, 5, and 8, the medical apparatus 10 comprises numerous signal connection outlets 46 of different format (including USB, Ethernet, DVI and other digital and analog interfaces) and a power supply outlet 48. The power supply outlet 48, if the medical apparatus is foreseen for the European market, is for example an outlet for an IEC plug to connect to an electrical power supply grid with, for instance, 230 volts and 50 Hertz It can be seen in particular in FIGS. 2, 5 and 8 that the housing 20 of the medical apparatus 10 comprises several fastening devices 51 on the base surface 21, which are presented in greater detail below with reference to FIG. 10.

FIGS. 1 through 8 show that the medical apparatus 10 comprises on its top side 19 a bow-shaped, in particular an arched, handle 52 for supporting the medical apparatus that extends beyond the top surface 29 of the housing but is configured as a single unit together with the housing 20 or a part of the housing 20. Because, as already mentioned, FIG. 6 shows a section along the plane A-A shown in FIG. 5, only cross-sections 53 of the handle 52 are visible in FIG. 6. Consequently, characteristics of the medical apparatus 10 that lie below the handle 52 are recognizable.

In particular in FIGS. 1 and 5 through 8, it can be seen that the medical apparatus 10, between the upper edge of the rear surface 24 of the housing 20 and the handle 52, comprises a pair of hook-shaped cable retainers 54 on which one or more cables can be wound when they are not needed. It is shown in the same figures that the medical apparatus 10 comprises a retainer device 56, 57 for a bottle or other container for a fluid used in an endoscopic investigation. The retainer device, as can be seen in particular in FIGS. 6 through 8, includes an arched bow 57, which partially encloses a cylindrical volume that is configured as another portion by a recess 56 that proceeds from the rear and top in the housing 20.

It can be seen in particular from FIGS. 7 and 8 that the rear surface 24 of the housing 20 in its U-shape surrounds approximately three sides of a recess 60 on the rear of the housing 20. Positioned in the recess 60 are an essentially rectangular cooling element 62 for removing heat effluents and, on the four corners of the cooling element, four pins, described in greater detail below with reference to FIG. 9, which form a fastening device 64. A few of the aforementioned signal connection outlets 46 are positioned between the cooling element 62 and the handle 52. The recess is partly closed off from above by the handle 52.

A light source 70 cited in FIGS. 2, 5, 7 and 8 is positioned in the housing 20 of the medical apparatus 10. The light source 70 can be serviced through a maintenance flap 71. In particular, a lighting element (halogen lamp, high-pressure gas discharge lamp, light diodes, etc.) can be replaced with the maintenance flap 71 open. A ventilation grid 72 for the light source 70 is positioned on the right side surface 27. A ventilation grid can also be mounted in the maintenance flap 71.

The medical apparatus 10 also includes a network portion 75 that is likewise only indicated in FIGS. 2, 5, 7 and 8 and that, for example, includes a transformer and electronic switches to generate and level one or more DC voltages to supply the light source 70 and other components of the medical apparatus 10.

In addition, the medical apparatus includes a pump 77, indicated in FIGS. 2, 5, 7 and 8, for pumping a fluid, and in particular air, to the coupling device 42. A pump 77 is taken here also to mean a thickener or blower or another device for advancing a compressible or non-compressible fluid. A silencer 76 on the suction side or at the inlet of the pump 77 is accessible via a maintenance flap 78 with a ventilation grid 79 or ventilation openings. Said silencer 76 can include a filter to filter the fluid suctioned by the pump 77 via the silencer 76.

It is clear in particular from FIGS. 3 and 4 that the front surface 23 and the rear surface 24 are not positioned in the right angle to the base surface 21. Instead the front surface 23 and rear surface 24 are inclined toward the rear 14 of the medical apparatus 10. For clarification, FIG. 3 shows a surface 81 of a table surface or another flat surface on which the medical apparatus 10 stands as well as a perpendicular 82 to the surface 81. The angle alpha between the front surface 23 and the perpendicular 82 in this embodiment lies between 8 and 9 degrees, in particular at 8.3 degrees.

Also shown in FIG. 3 is a center of mass 84 of the medical apparatus 10. Especially because of the inclination of the front surface 23 and of the proportionately heavy screen 32 in it, as well as because of the low placement of the light source 70, of the network portion 75 and of the pump 77, it is possible to position the center of mass 84 at a short distance from the base surface 21. In particular, the distance s of the center of mass 84 from the base surface 21 is at most one-third, better yet at most one-fourth, of the height h (measured perpendicularly to the base surface 21) of the housing 20 (without the handle 52). In addition, the distance of the point of intersection of the perpendicular through the center of mass 84 onto the base surface 21 from the lines of intersection of the plane defined by the base surface 21 with the planes defined by the front surface 12 or rear surface 24 is each at least one-third of the distance of the front surface 23 and rear surface 24 measured parallel to the base surface 21.

To place the center of mass in this position, the light source 70, network portion 75 and pump 77 are positioned in such a way that the areas occupied by them extend only over the lower half or less, or better yet over the lower two-fifths or less of the height h of the housing 20.

Shown in FIG. 6 are the perpendicular 86 on the front surface 23 of the housing 20 and a direction 87 of the coupling device 42. The direction 87 of the coupling device 42 is the direction in which a coupling of a light conductor cable or a coupling on a proximal end of an endoscope can be inserted into an adapter device 44 in the coupling device 42. The angle beta between the direction 87 and the perpendicular 86 measures about 60 degrees.

FIG. 4 shows the medical apparatus 10 with a transport case 90 for protected transport of the medical apparatus 10. The transport case 90 comprises a lock 91 for locking the case. Fastening devices 93 that are complementary to the fastening devices 51 on the base surface 21 are positioned on an outer surface 92 of the transport case 90. Said fastening devices 93 on the transport case 90 can end flush with the outer surface 92 or, as indicated in FIG. 4, can extend partly to the outside with respect to it. An example of a fastening device 51 on the bottom surface 21 of the housing 20 of the medical apparatus 10 and a complementary fastening device 93 on the transport case 90 is shown below with reference to FIG. 10.

The medical apparatus 10 is shown in FIGS. 5 and 8 secured on a bracket with a plate 96 and an arm 97. The bracket 96, 97 is, for example, a part of a wall and ceiling bracket. The plate 96 comprises four bored throughholes that comply with the VESA standard for wall and ceiling brackets for flat screens. One screw 99 each is screwed through one of these boreholes in the plate 96 in a threaded hole 66 or a borehole with inner thread of the fastening device 64, although only one of the screws 99 is shown in FIG. 8. Alternatively a battery can be removably secured on the fastening device 64. For this purpose, in addition, a catch-groove 68 in the form of U-shaped recesses or notches is configured in several ribs of the cooling element 62, which can be seen in particular in FIGS. 2 and 7. This is described more fully below with reference to FIG. 9.

Figure 9:
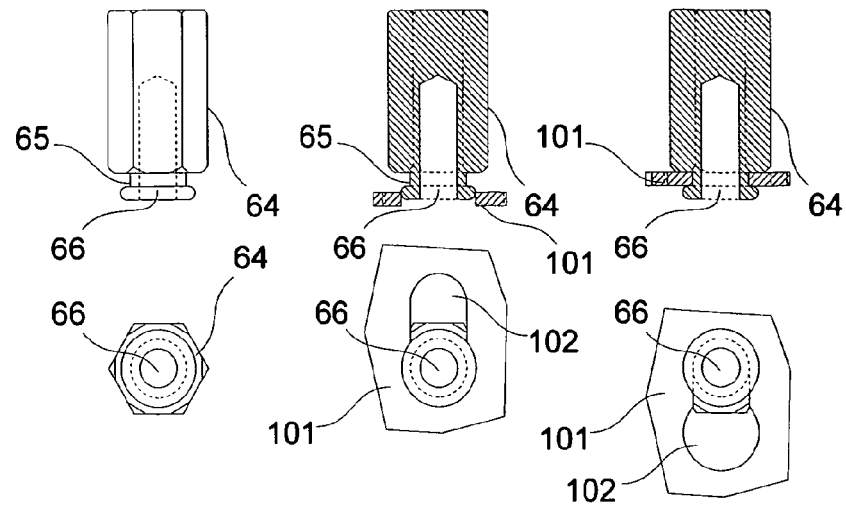
FIG. 9 shows a schematic depiction of a fastening device for an accumulator of the medical apparatus.

FIG. 9 shows schematic depictions of one of the four equal components of the fastening device 64 in the recess 60. The fastening device 64 comprises a tapered shape 65 or a part with reduced cross-section and a threaded borehole 66. A screw 99 can be inserted into the threaded borehole 66 in order to securely screw the fastening device 64 on the plate 96 of the bracket as described above with reference to FIGS. 5 and 8. Alternatively a housing wall 101 of a battery, of which only a small portion is shown in FIG. 9, can be suspended with a keyhole-shaped recess 102 in the fastening device 64. FIG. 9, in the center, shows how the keyhole-shaped opening 102 is moved by the fastening device 64; at right the housing wall 101 is shown suspended in the fastening device 64. Thus the center and right section each shows, in the upper area, a section parallel to the axis of the fastening device 64 and, below, an overhead view in the direction parallel to the axis of the fastening device 64.

A catch-lock nub can be positioned on the housing wall 101 facing the cooling element 62 and the fastening devices 64 of the battery. In the position of the housing wall 101 relative to the fastening device 64 shown at right in FIG. 9, the catch-lock nub of the battery engages in the catch-lock groove 68 that can be seen in FIGS. 2 and 7. The battery is thus kept catch-locked in the position shown at the right in FIG. 9 to prevent unintentional release of the fastening devices 64. To remove the battery from the fastening devices 64, the catch-locking is undone, for example by a corresponding force. Alternatively a lever or another device is provided on the battery with which the catch-locking nub of the battery can be pulled out of the catch-lock groove 68.

In the embodiment shown above in FIGS. 2 and 5 through 9, the fastening device 64 holds the cooling element 62 simultaneously in the recess 60. In particular, the fastening device 64 is executed in the form of hexagonal columns which are screwed onto the housing 20 of the medical apparatus 10 by means of a suitable tool. The fastening device 64 can thus simultaneously hold the cooling element 62, in that the screw-in connections grip through openings or through-holes in the cooling element between the columns of the fastening device 64 and the housing. Alternatively, contrary to the depiction in FIGS. 2 and 5 through 9, the cooling element is removably secured on the fastening device. In the process, the fastening device and cooling element can be configured in such a way that the cooling element and a battery can be alternatively or simultaneously removably secured on the fastening device in the recess.

Figure 10:
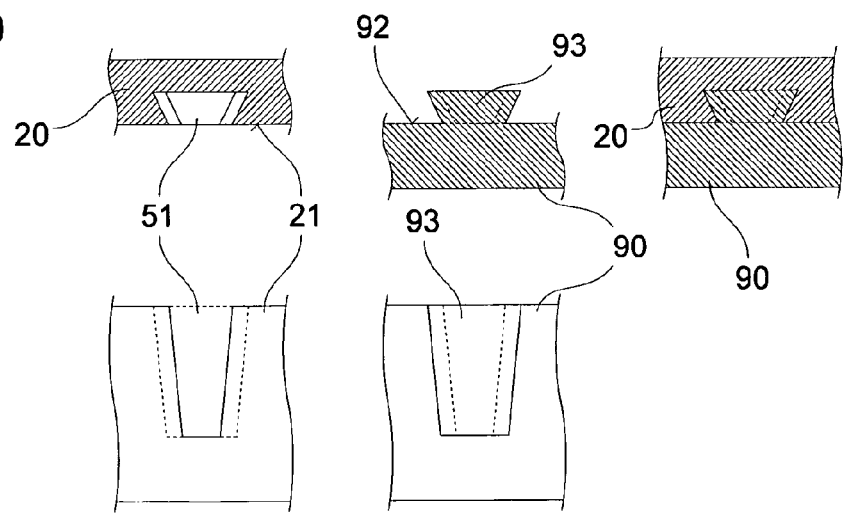
FIG. 10 shows schematic depictions of a fastening device to removably secure the medical device on a transport case.

FIG. 10, at left and in the center, shows depictions of the fastening device 51 on the base surface 21 of the housing 20 of the medical apparatus or of the fastening device 93 on an outer surface 92 of the transport case 90. Here, in each case, a cross-section is shown above and an overhead view below. Shown at the right in FIG. 10 is a cross-section of the fastening devices 51, 93 that are mechanically connected with one another and by which the base surface 21 of the housing 20 of the medical apparatus 10 is mechanically connected with the transport case 90.

The fastening device 51 is a groove with a dovetail-shaped or trapezoidal cross-section, such that the cross-section declines from one end of the groove to the other. The fastening device 93 on the outer surface 92 of the transport case 90 is a stud with a dovetail-shaped or trapezoidal cross-section, which becomes smaller from one end of the stud to the other. The cross-sections of the groove 51 and of the stud 53 are adapted to one another or complementary to one another. If the stud 93 is pushed into the groove 51 as shown in FIG. 10 at right, there is a form-locked mechanical connection between the housing 20 of the medical apparatus 10 and the transport case 90 in the direction perpendicular to the base surface 21.

Figure 11:
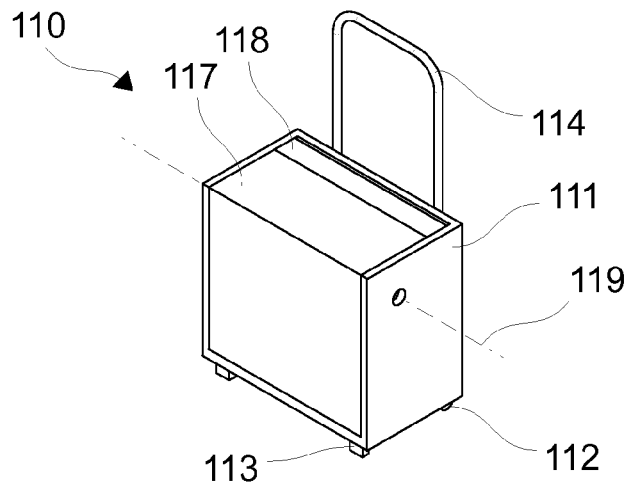
FIG. 11 shows a schematic depiction of a transport case for a medical apparatus.
Figure 12:
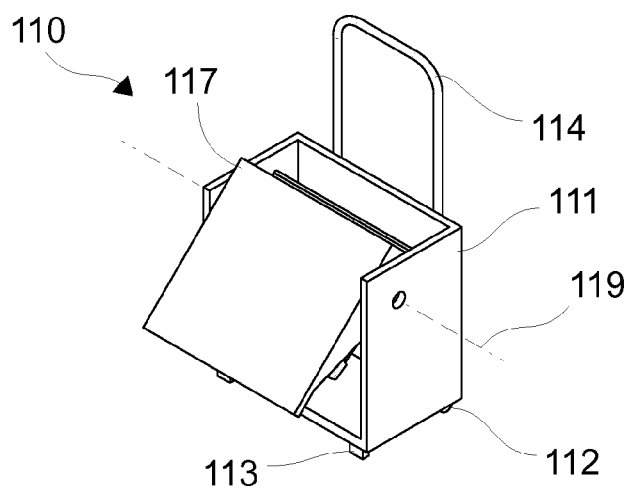
FIG. 12 shows another schematic depiction of the transport case.
Figure 13:
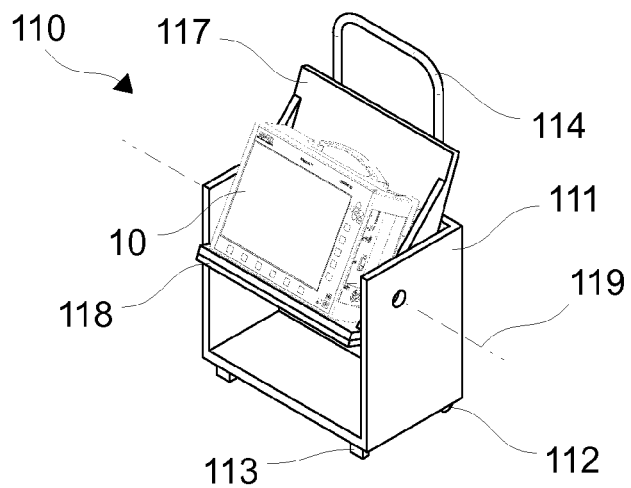
FIG. 13 shows another schematic depiction of the transport case with the medical apparatus.

FIGS. 11, 12 and 13 present schematic axonometric depictions of a transport case 110 for the medical apparatus 10 presented above with reference to FIGS. 1 through 8. The transport case 110 comprises a first hull 111 that includes four essentially flat and essentially rectangular sections. Positioned near the four corners of the first hull, which are closely situated and essentially lying in a single plane, are two wheels 112 and two rigid feet 113 on which the first hull 111 can be supported on a flat underground base. Only one of the two wheels 112, which can rotate around the same axis, is visible in each of FIGS. 11 through 13. If the transport case with the two wheels 112 and two feet 113 rests on a flat underground base that does not depart too strongly from the horizontal, friction between the rigid feet 113 and the base prevents any motion of the transport case 110 parallel to the foundation.

In addition, a rigid or telescopically expandable bow-shaped handle 114 is positioned on a rectangular portion of the first hull 111, near whose border the two wheels 112 are positioned facing away from the handle 114. The transport case 110 can be tipped by means of the handle 114 in such a way that it is only supported on the underground base with the wheels 112 but no longer with the feet 113, and can then be pulled and pushed over the base with little resistance to rolling.

In addition, the transport case 110 comprises a second hull 117, which includes two L-shaped sections adjacent to one another that are essentially flat and essentially rectangular. A strip-type section 118 on the border of the second hull 117 is movable with respect to the rest of the second hull 117. The second hull 117 can rotate with respect to the first hull 111 around an axis 119. In the position of the second hull 117 shown in FIG. 11, the second hull 117 closes a corresponding opening formed in the first hull 111, and the first hull 111 and second hull 117 form a closed receptacle.

After a folding down of the strip-type section 118, the second hull 117 can be pivoted around the axis 119, from the position shown in FIG. 11 through the position shown in FIG. 12 to the position shown in FIG. 13.

The medical apparatus 10 presented above with reference to FIGS. 1 through 8 and 11 through 13 can be removably secured inside on the L-shaped second hull 117, for example in similar manner as shown above in FIG. 10. The medical apparatus 10 can remain constantly secured on the second hull 117, both during transport and also during its use in an endoscope. During transport the second hull 117 is bolted into the position shown in FIG. 11. The first hull 111 and second hull 117 surround the medical apparatus 10 completely and protect it from environmental impacts. After a pivot or rotation of the second hull 117 around the axis 119 into the position shown in FIG. 13, the medical apparatus 10 is immediately usable without having to be removed from the second hull 117.

The securing of the medical apparatus 10 on an outer surface 92 of a transport case 90 or on a plate 96 of a wall or ceiling bracket or in a transport case 110 was described with reference to FIG. 3 or 5 and 8 or 11 through 13. Alternatively or in addition, the medical apparatus 10 can be configured so as to be secured by means of the fastening devices 51 on its base surface and/or by means of the fastening devices 64 in its recess 60 on a shelf or fastening device according to the VESA standard on a mobile or stationary shelf or device holder or on a base plate.

What is claimed is:

1. A medical apparatus to support an endoscopic intervention, comprising:
    a housing with a base surface, a top surface, a front surface and a rear surface, the base surface, top surface, front surface, and rear surface defining an enclosed area, the front surface having a surface area greater than a surface area of the base surface;
    a light source positioned in the housing, the light source generating light to illuminate an object that is to be investigated with an endoscope;
    a coupling device coupling a proximal end of the endoscope to the medical apparatus and transmitting light from the medical apparatus to the endoscope;
    a screen integrated in the front surface of the housing, the screen displaying an image captured by the endoscope;
    where the front surface and rear surface are each fixed in position relative to the base surface and are each inclined toward a rear of the housing by an angle between 5 and 15 degrees with respect to a plane perpendicular to the base surface;
    wherein a height of the housing from the base surface and a width of the housing are each greater than depth of the housing, the depth being a distance between the rear surface and the front surface along the base surface, and the width being a distance between sides surface of the housing.

2. The medical apparatus according to claim 1, wherein the coupling device is positioned at an angle between 50 and 70 degrees to the front surface.

3. The medical apparatus according to claim 1, wherein the light source is positioned in an area of the housing bordering the base surface.

4. The medical apparatus according to claim 1, further comprising:
    a fastening device on the base surface to secure the housing at least either on a transport case for the medical apparatus or on a tripod or other device.

5. The medical apparatus according to claim 4, further comprising:
    a transport case that is configured to contain the medical apparatus, wherein a fastening device on the transport case and the fastening device on the base surface of the housing of the medical apparatus are configured to removably connect with each other.

6. The medical apparatus according to claim 5, wherein the fastening device on the base surface of the housing includes at least a groove or a stud with a dovetail-shaped or trapezoidal cross-section, and wherein the fastening device on the transport case is complementary to the fastening device on the base surface of the housing and accordingly includes at least a stud or a groove with dovetail-shaped or trapezoidal cross-section.

7. The medical apparatus according to claim 1, wherein the rear surface has a U-shape surrounding a recess, said recess having at least one fastening device positioned therein to secure at least one of a battery and a cooling element on the medical apparatus.

8. The medical apparatus according to claim 7, wherein the fastening device in the recess is configured to simultaneously secure the battery and the cooling element on the medical apparatus.

9. The medical apparatus according to claim 7, wherein the cooling element disposed in the recess is adapted to divert heat effluents from at least one of the light source, a power supply integrated into the medical apparatus, and additional devices integrated into the medical apparatus.

10. The medical apparatus according to claim 1, further comprising:
a cable bracket on the rear of the housing to store a cable for the medical apparatus.

11. The medical apparatus according to claim 1, wherein a center of mass of the medical apparatus is positioned at most one-third of a height of the housing from the base surface.

12. The medical apparatus according to claim 1, further comprising:
a bracket device, which is partly integrated into the housing, to hold a receptacle for a fluid that is to be used during an endoscopic investigation.

13. The medical apparatus according to claim 7, wherein the fastening device in the recess is configured to alternatively or simultaneously secure the medical apparatus on a bracket.

14. The medical apparatus according to claim 1, wherein the front surface and rear surface are each inclined toward the rear of the housing by an angle between 7 and 10 degrees with respect to the plane perpendicular to the base surface.

15. A medical apparatus to support an endoscopic intervention, comprising:
a housing with a base surface, a top surface, a front surface and a rear surface, the base surface, top surface, front surface, and rear surface defining an enclosed area;
a light source positioned in the housing, the light source generating light to illuminate an object that is to be investigated with an endoscope;
a coupling device coupling a proximal end of the endoscope to the medical apparatus and transmitting light from the medical apparatus to the endoscope;
a screen integrated in the front surface of the housing, the screen displaying an image captured by the endoscope;
where the front surface and rear surface are each fixed in position relative to the base surface and are each inclined toward a rear of the housing by an angle between 5 and 15 degrees with respect to a plane perpendicular to the base surface;
the rear surface having a U-shape surrounding a recess, said recess having at least one fastening device positioned therein to secure at least one of a battery and a cooling element on the medical apparatus;
wherein the fastening device has a tapered shape and the battery has a housing wall with at least one key-shaped recess, the key-shaped recess being adapted to suspend on the tapered shape of the fastening device; and
wherein the cooling element comprises a catch-lock groove adapted to provide connection with the battery.

\* \* \* \* \*